United States Patent
Selner

(10) Patent No.: US 10,159,704 B2
(45) Date of Patent: Dec. 25, 2018

(54) PENETRATING CARRIER, ANTI-FUNGAL COMPOSITION USING THE SAME AND METHOD FOR TREATMENT OF DERMATOPHYTES

(75) Inventor: Marc Selner, Studio City, CA (US)

(73) Assignee: POWER PHARMACEUTICALS, LLC, Studio City, CA (US)

( * ) Notice: Subject to any disclaimer, the term of this patent is extended or adjusted under 35 U.S.C. 154(b) by 33 days.

(21) Appl. No.: 12/568,833

(22) Filed: Sep. 29, 2009

(65) Prior Publication Data
US 2010/0035939 A1    Feb. 11, 2010

Related U.S. Application Data

(63) Continuation-in-part of application No. 11/684,869, filed on Mar. 12, 2007, now Pat. No. 7,601,371, and a continuation-in-part of application No. 10/956,073, filed on Oct. 4, 2004, now Pat. No. 7,597,913.

(60) Provisional application No. 61/194,508, filed on Sep. 29, 2008.

(51) Int. Cl.
| | | |
|---|---|---|
| A61K 36/16 | (2006.01) | |
| A61K 36/54 | (2006.01) | |
| A61K 36/23 | (2006.01) | |
| A61K 36/53 | (2006.01) | |
| A61K 36/537 | (2006.01) | |
| A61K 36/61 | (2006.01) | |
| A61K 36/87 | (2006.01) | |

(52) U.S. Cl.
CPC .............. *A61K 36/54* (2013.01); *A61K 36/16* (2013.01); *A61K 36/23* (2013.01); *A61K 36/53* (2013.01); *A61K 36/537* (2013.01); *A61K 36/61* (2013.01); *A61K 36/87* (2013.01)

(58) Field of Classification Search
None
See application file for complete search history.

(56) References Cited

U.S. PATENT DOCUMENTS

| | | | |
|---|---|---|---|
| 4,933,175 A | 6/1990 | Passarelli | |
| 5,000,954 A | 3/1991 | Stadtmueller | |
| 5,264,206 A * | 11/1993 | Bohn et al. | 424/61 |
| 6,344,190 B1 | 2/2002 | Nair et al. | |
| 6,380,236 B2 * | 4/2002 | Glassman | 514/399 |
| 2005/0014730 A1 | 1/2005 | Carlson et al. | |
| 2006/0120977 A1 | 6/2006 | Friedman et al. | |
| 2007/0160551 A1 | 7/2007 | Selner | |

FOREIGN PATENT DOCUMENTS

| | | | |
|---|---|---|---|
| GB | 191127348 A * | 9/1912 | |
| WO | WO 02/22115 A2 | 3/2002 | |

OTHER PUBLICATIONS

Graedon et al. "People's Pharmacy Skin Improves with Vicks VapoRub" from The Baltimore Sun Article Collections. Apr. 30, 2000 [Retrieved from the Internet on: Jun. 13, 2011].*
Yu et al. "A clinical and laboratory study of ciclopirox olamine (8% Batrafen) in the treatment of onychomycosis." Chin Med Sci J, vol. 6, No. 3 (Sep. 1991) 166-168, Abstract only.*
Lilenthal, S. "Onychomycosis" from "A Treatise of Diseases of the Skin". New York: Boericke & Tafel. 1876, p. 183.*
Gupta et al. Journal of the American Academy of Dermatology. vol. 43, Issue 4, Supplement, Oct. 2000, pp. S70-S80.*
(U1) Ramsewak et al. Phytother. Res. 17, 376-379 (2003).*
European Office Action dated Mar. 28, 2011, in Patent Application No. 05 735 368.2.
Summons to attend oral proceedings issued Feb. 13, 2012 in Europe Application No. 05735368.2.

* cited by examiner

*Primary Examiner* — Amy L Clark
(74) *Attorney, Agent, or Firm* — Oblon, McClelland, Maier & Neustadt, L.L.P.

(57) ABSTRACT

An antifungal liquid composition for topical administration is provided that contains turpentine and at least one of peppermint oil, mineral oil, and essential oil alcohols, and one or more antifungal medications selected from ciclopirox olamine, terbinafine, tolnaftate, microconazole, itraconazole, ketoconazole, econazole, and fluconazole, and optionally one or more antifungal essential oils, and its use in the topical treatment of fungal infection, particularly of the nail.

22 Claims, No Drawings

US 10,159,704 B2

PENETRATING CARRIER, ANTI-FUNGAL COMPOSITION USING THE SAME AND METHOD FOR TREATMENT OF DERMATOPHYTES

INFORMATION REGARDING RELATED APPLICATIONS

This application is a Continuation-in-Part of U.S. application Ser. No. 10/956,073, filed Oct. 4, 2004, and is a Continuation-in-Part of U.S. application Ser. No. 11/684,869, filed Mar. 12, 2007, and further claims priority to U.S. Provisional Application Ser. No. 61/194,508, filed Sep. 29, 2008, the entire contents of each of which are hereby incorporated by reference.

BACKGROUND OF THE INVENTION

Field of Invention

The present invention relates to a carrier for a topical medicament having improved ability to penetrate thick keratinous tissues, a topical anti-fungal composition useful for the treatment of dermatophytes infection in the nail bed and nail plate and a method for treating fungal nail infections using the composition.

Discussion of the Background

Dermatophytes are filamentous fungi that are commonly found in plants and soil. Nail invasion by these organisms cause disease, with thickening, discoloration, odor, decay, lysis (loosening of the nail plate from the base of the nail bed), and deformity such as increased curvature of the nail plate. In addition to dermatophytes, candida albecans (a yeast) is also a common pathogen. A small number of diseases are also caused by molds, considered non-dermatophytes. The medical name for fungal nail disease is onychomycosis. Fungi live in the nail bed under the toenail and also involve the nail itself. The fungus is a parasite, and lives on the keratin, by dissolving the keratin with enzymes known as keratinases. The most common organisms are Trichophytan Rubrum (which causes between 80-90% of infections), Trichophytan Mentagrophytes, Epidermophytan Floccosum and Candida Albecans.

Many times the fungi will cause the nail to produce excess keratin, a condition known as hyperkeratosis, causing the nail to be thicker and often deformed. Additionally, the thicker toenail can cause pain, leading to ingrown nails, and even difficulty in wearing shoes due to the thickness. The typical treatment for this condition involves having a podiatrist debride or manually thin the nail, often at great cost to the patient, insurance, and Medicare.

The cells in the nail are connected by a intercellular phospholipid connections called desmosome. To effectively treat onychomycosis, it is necessary to get the antifungal medicine through the nail plate and keratin, which may be very thick, and penetrate to the site where the organism lives.

One U.S. study suggested a prevalence of Onychomycosis of 18.5% with the number of persons affected on the rise, which may be partly accounted for by the aging U.S. population. Onychomycosis affects 32% of the people between 60-70 years of age, and some studies suggest it may affect 48% of the population by age 70. Onychomycosis has a stronger prevalence in immunosuppressed people, such as those with diabetes, poor circulation, or HIV infection. Toenail infections are several times more common than fingernail infections. Several oral medicines are effective in treating these conditions, such as Lamisil and Sporonox. However, these medicines are prescription medications, costing the patient as much as $1000 to treat an infection, and requiring extraneous lab tests, because they can cause damage to the liver and kidneys as well as other side effects.

Topical treatments have historically been somewhat ineffective. According to the Physicians Desk Reference, antifungals used for skin, such as terbinafine (Lamisil), Ciclopirox Olamine and tolnaftate, are not indicated topically for fungal toenails because they don't penetrate. While Ciclopirox Olamine is FDA approved for toenail, it is in a water soluble lacquer (Penlac) and therefore doesn't penetrate more than approximately 0.4 mm through the large toenail. Because of this, Penlac requires monthly treatments by the doctor to debride or remove the dead nail tissue and is expensive (with a small bottle of 6 cc costing typically over $150). Additionally it is only indicated for disease of the nail distal to the lunula-white half moon. According to the Physician's Desk Reference (PDR), studies using Penlac indicate only about a 10% cure rate and about 50% improvement. Further, the PDR states that Penlac is not effective against the most common fungus to infect nails, Trichophytan Rubrum.

In order to get effective concentrations of terbinafine, it is necessary to administer it orally. The pills are often expensive and require doctor's visits to monitor liver toxicity. One in 500 patients has a serious reaction to the drug. In addition to this, there is a 15% reoccurrence of the fungal toenail in the first year. There are other OTC medicines but proof of their efficacy is difficult to determine.

SUMMARY OF THE INVENTION

Accordingly, one object of the present invention is to provide a carrier for topical medicaments that can penetrate and transport a broad spectrum of antifungal compounds through keratinous tissues, such as nail bed and nail plate.

A further object of the present invention is to provide a topical composition for treatment of fungal infections using this carrier.

A further object of the present invention is to provide a topical anti-fungal composition effective at treating onychomycosis.

A further object of the present invention is to provide a topical anti-fungal composition that requires no debridement during treatment.

A further object of the present invention is to provide a method for the topical treatment of nail infections using such anti-fungal compositions.

These and other objects of the present invention, either alone or in combinations thereof, have been satisfied by the discovery of an antifungal liquid composition for topical administration, comprising:

a carrier system comprising a turpentine and at least one member selected from peppermint oil, mineral oil and essential oil alcohols; and an effective amount of one or more active agents selected from the group consisting of ciclopirox olamine, terbinafine, tolnaftate, microconazole, itraconazole, ketoconazole, econazole, and fluconazole;

and its use in the topical treatment of fungal infections, particularly of the nail.

DETAILED DESCRIPTION OF THE INVENTION

The present invention relates to a liquid carrier system comprising combination of turpentine (pine oil) and at least one of peppermint oil, mineral oil, or essential oil alcohols. When combined with one or more active ingredients, this carrier system provides penetration of keratinous tissue and transport and delivery of the active ingredient to the site in need thereof.

The present invention further relates to an topically applied anti-fungal composition, comprising:

an effective anti-fungal amount of one or more members selected from the group consisting of ciclopirox olamine, terbinafine, tolnaftate, microconazole, itraconazole, ketoconazole, econazole, and fluconazole, and the above noted liquid carrier system.

In a preferred embodiment, the composition comprises an effective anti-fungal amount of a mixture of ciclopirox olamine and terbinafine, and optionally tolnaftate, along with the liquid carrier system. In a further preferred embodiment, the composition comprises an effective anti-fungal amount of a mixture of ciclopirox olamine, terbinafine, tolnaftate, and fluconazole, along with the liquid carrier system.

The keratin that forms toenails has fat channels made of cholesterol, fatty acids and fat found in nerves. The present inventor has found that in order to penetrate the nail, one must use a fat soluble carrier in a fat miscible solution to carry completely through the nail and into the nail bed where the fungus lives. Anything short of this clinically and it doesn't work.

The antifungal composition of the present invention is preferably in the form of a liquid, containing one or more antifungal medications in a proven carrier. The fat soluble carrier system of the present invention comprises a combination of turpentine (pine oil) and at least one of peppermint oil or mineral oil. This carrier system is one important aspect of the present invention, as it provides the ability to take the fat soluble substances and penetrate the thick keratin layer of the nail in an effective manner. The use of the one or more antifungal medications selected from ciclopirox olamine, terbinafine, microconazole, itraconazole, ketoconazole, econazole, and tolnaftate, has been found to be effective on most or all of the different types of fungal infections of the nail (particularly the toenail) in a broad spectrum, particularly preferably when used in a combination of ciclopirox olamine, terbinafine and tolnaftate. Additionally, the composition can optionally contain an effective amount of Fluconazole for onychomycosis brought about by a yeast infection. Further, the combination preferably helps overcome the resistance of the different fungi as they mutate and change in an attempt to avoid being destroyed. The composition is preferably in a liquid form, since liquids have the best penetration. Further, the composition is most preferably in a liquid carrier that is a non evaporative substance, particularly preferably the carrier system of the present invention. With evaporation, the carrier tends to disappear before it can penetrate the thick nail plate.

In a most preferred embodiment, the carrier of the present invention, when put on a non absorbtive material, does not significantly evaporate over a period of days, and most preferably has essentially a negligible vapor pressure under normal atmospheric conditions, thus exhibiting no observable evaporation to any significant extent.

The conventional approach to treatment of nail fingus is to debride the nail manually to remove as much of the keratin caused by the thickening of the fungus, in order that penetrations of antifungal medicines can result. Additionally application of antikeratolytics, such as salicylic acid or urea, are also used to remove keratin debris. The reason for this is that keratin is layered as a protective shield against penetration of substances. It is found in the skin as well. Some conventional products use various substances to enhance penetration with limited success such as alcohol, polyethylene glycol, triglycerides, fatty acids, liposomes, nanospheres, or lecithin. These all have limited ability to penetrate the skin and are essentially of no use on a thick layer of keratin in toenails. Because the cell membranes are made of phospholipids, fat soluble substances can pass between cells called desmosome connections, through cell membranes and through keratin. U.S. Pat. No. 6,344,190 discloses a composition for treatment of dermatophytes that contains several essential oil components and a carrier system. However, the disclosed compositions do not teach a carrier system or combination of specific essential oils such as required in the present invention composition. Namely, the only carrier systems specifically named in the '190 patent appear to be an alcohol ester, such as isoamyl alcohol (an evaporative carrier) or a commercially available product designated VICKS VAPO-RUB (a thick greasy carrier system containing a mixture of unidentified ingredients).

The present invention composition and method use a carrier that penetrates the keratin by being a fat soluble substance, such as hydrocarbons. A preferred carrier is a combination of turpentine (pine oil) and at least one of peppermint oil or mineral oil. In a more preferred embodiment, the carrier comprises the combination of turpentine, peppermint oil and mineral oil. This preferred combination of three carrier components helps to pull the antifungal medications of the present invention antifungal composition through the thick layers of keratin found in the nail. The present composition does not require debridement of the nails or keratolytics in order to be effective. The present composition has been found effective in treating nail fungus just by application directly to the nail surface on a regular basis. However, while not requiring the above, the present composition can be used in combination with debridement or added keratolytics, if desired.

To reach the desired area the carrier must be fat soluble (i.e., will dissolve in fat, remain soluble and forms an essentially homogeneous solution with fat) and the antifungal agents must also be fat soluble to penetrate these intercellular fat soluble connections, as well as the keratin. To be effective, the formula must have the ability to penetrate the toenail. Most conventional antifungal compositions are not effective on toenails (absent debridement or keratolytics) because they are not able to get the antifungal composition thru the nail plate and skin under the nail called the nail bed.

The present composition has been found to be effective on substantially all types of nail fungus disorders, whether of distal type, lateral type, superficial type, or proximal type involving the whole nail. Studies using sequential photography have shown its effectiveness as over 65% cure/improvement. Importantly, the present composition does not require debridement of the nail to be effective, because the vehicle for penetration of the nail plate works regardless of the thickness of the nail. The composition is also broad spectrum, which is necessary because these organisms are polymorphic and can change their resistance. The combination of multiple effective antifungal essential oils in the present composition allow for this. While the preferred use for the present composition is treatment of onychomycotic toenails, the composition can be used to treat skin fungus infections as well. Upon treatment of nail fungus with the present composition, it has been noted that the nails appear to grow faster as treatment progresses. This may be due to increased nail growth as a result of decreasing the fungal involvement, or by stimulation of the nail matrix by the present composition.

The present composition can be in any form suitable for topical application, particularly to the nail surface. The composition can preferably take a form including, but not limited to, liquid solutions, liquid suspensions, liquid dispersions, gels, jellys, cremes, and ointments. Most preferably for application to the nail, the composition is in the form of a liquid, either solution, suspension or dispersion. For use on skin, either liquid or gel/jelly forms are preferred. In use on skin, the composition preferably contains petrolatum as an additional carrier. The petrolatum may be as is, or may be treated with ultraviolet light (preferably using a cold UV lamp), which has been reported to provide additional healing properties through a property called "radiolatum".

Although not required in the present composition, the composition can optionally contain one or more keratolytic agents, such as salicylic acid or urea, as well as other conventional additives and/or auxiliaries used in topical compositions. Such conventional additives or auxiliaries include, but are not limited to, fillers, colorants or dyes, skin conditioners, MSM (methylsulfoxymethane), etc.

Nail fungi are parasites that live and grow in the nail and underlying skin called nail bed. The fungus lives off the keratin of the nail and causes the nail to produce more keratin. The fungus produces spores and tentacles called hyphae that grow out. The fungus also produces keratinases to eat away at the keratin as well. The keratin is a protein, and like the outside layer of the skin, tends to prevent things from penetrating. When the fungus does invade the toenail, it eats away and rots it, much like a rotting piece of wood. While plants and trees have natural antibiotic oils in their leaves and bark, to keep away these invaders, human tissue does not have the same advantage. Based on this principal, the present composition uses a mixture of antifungal medications. However, the medications alone still have a difficult time penetrating the thick keratin nail plate. Prior to the present invention, so far as is known by the present inventor, no one has found a way to do this effectively as a topical agent. With the present invention composition, the antifungal medications are carried or delivered through this tough, up to now impenetrable, barrier. The present composition provides a mixture of antifungal medications that is a broad spectrum antifungal combination so as to cover all the mutant resistances that develop, prevents keep the fungus from growing, and is not harmful to the nail or nail matrix.

The present invention carrier or delivery system comprises a combination of turpentine (pine oil) and at least one of peppermint oil or mineral oil or one or more essential oil alcohols. Suitable essential oil alcohols include, but are not limited to, menthol, eugenol, eucalyptol, cinnamyl alcohol, linalool, charvicol (methyl charvicol), terpinols anethole, geraneol, and terpinols.

The optional antifungal essential oils are preferably plant extracts and are fat soluble. The composition optionally comprises a mixture of antifungal essential oils comprising one or more members selected from camphor, eucalyptus globulus, cedarwood oil, Manuka oil, sage oil, juniper oil, clove oil, lavender oil, cinnamon bark and leaf oil, grapeseed oil, jojoba oil, anise oil, neem oil, rosewood oil, eucalyptus citroidia, and nutmeg oil. Importantly, the antifungal essential oils used are preferably substantially free of the presence of thymol. Within the context of the present invention, the term "substantially free of thymol" is used to indicate that the essential oils used do not have detectable amounts of thymol, as determined by gas chromatographic analysis of the essential oil itself. In one embodiment of the present invention, the composition further comprises grapeseed extract and anise oil, which together increase effectiveness of the composition against yeasts known as polygyols, potentially up to a 30-40 fold increase in effectiveness.

The amount of each antifungal essential oil used is preferably in the range of from 0.1% to 40%, based on total composition amount. More preferably, the antifungal essential oils are present in an amount of from 0.1% to 10%, most preferably from 1% to 5%, based on total composition amount. These amounts do not have to be the same for each antifungal essential oil, and the amount of each individual essential oil present in the composition is independent of the identity or amount of other components used.

The amount of each antifungal medication used is preferably in the range of from 0.1% to 40%, based on total composition amount. More preferably, the antifungal medications are each present in an amount of from 0.1% to 10%, most preferably from 1% to 5%, based on total composition amount. These amounts do not have to be the same for each antifungal medication, and the amount of each individual medication present in the composition is independent of the amount of other components used.

The carrier components are preferably each, independently, present in amounts of from 0.1-95% by weight, based on total composition amount. More preferably, the mineral oil is present in an amount of from 1-95% by weight. The turpentine and peppermint oil can also be in similar amounts as mineral oil. The carrier system itself can be used for delivery of any desired fat soluble active agent(s), particularly for treatment of disorders related to keratinous tissues.

One problem in treating fungal nail infection in women is that up to now it has been necessary for the women to remove their nail polish. The present composition, on the other hand, can be readily mixed into commercial nail polish of either enamel or oil based types (typically in the amount of 5 to 20 drops per 2.5 oz bottle of polish). While this results in a slight thinning of the polish, it can be readily applied and after drying appears as normal nail polish, while delivering the antifungal medication directly to the nail, through the nail and to the nail bed.

In preparing a preferred embodiment of the composition, it is preferred that the carrier system be combined with one or more of the ciclopirox olamine, terbinafine and tolnaftate, then upon addition of fluconazole, the entire mixture is heated at a temperature of from 100-150° F. to fully dissolve the fluconazole. The terbinafine is preferably used as terbinafine HCl. In a most preferred embodiment, the ciclopirox olamine is dissolved in the carrier system, followed by terbinafine HCl. (this appears to work best in this order, as it is believed that alcohol present in commercially available ciclopirox olamine helps to dissolve the terbinafine HCl). This is then followed by tolnaftate and/or econazole (if desired) and fluconazole as above, in the case of onychomycosis caused by yeast. When fluconazole is included, it is most preferred that the fluconazole be added to a small amount of the combination of carrier and antifungal essential oils, then heated at a temperature of from 100-150° F. to fully dissolve the fluconazole, then the resulting mixture combined with a mixture of the remainder of the carrier, essential oils and other antifungal medications.

The method for using the present composition comprises application of the composition directly to the nail surface. Preferably, the applications are performed from 1 to 4 applications per day, and are continued until the infection is eliminated, preferably for a period of several days to 12 months. Afterward, the composition can be used on a regular basis to prevent reoccurrence of the infection and encourage nail health. More preferably, the composition is applied from 1 to 2 times per day directly to the nail surface, most preferably immediately after bathing. The application is performed using any type of applicator, including but not limited to, fingers, brushes, swabs, etc. The application should preferably be sufficient to form a thin film of the composition on most or all of the nail surface. While the application can also include the skin area surrounding the nail, this can cause temporary skin irritation in some patients.

EXAMPLES

Based on application to a patient group of over 150 patients, application of the antifungal composition of the present invention gave a conservative estimate of 40-60% cure, with a rate of cure/improvement in the 66-85% range. Patients were instructed to apply the composition twice daily after bathing, then were individually observed on a monthly basis. Pictures can be taken to document recovery. If complete nail involvement was present, the total nail may take up to 9-12 months to grow out. Less involvement takes a shorter period of time, typically ⅓-½ of the time.

A most preferred example of the present antifungal composition contains the following:
A carrier system and essential oils composition of:

| Carrier System | |
|---|---|
| Mineral oil | 12.5% |
| Turpentine (pine oil) | 5% |
| Essential Oils | |
| *Eucalyptus globulus* | 5% |
| Peppermint | 5% |
| Cedarwood | 5% |
| Manuka | 5% |
| Sage | 5% |
| Juniper | 5% |
| Clove | 5% |
| Lavender | 5% |
| Cinnamon bark and leaf oil | 5% |
| Jojoba oil | 5% |
| Grapeseed | 5% |
| Anise | 5% |
| Tea Tree | 5% |
| Rosewood | 5% |
| *Eucalyptus citroidia* | 2.5% |
| Nutmeg | 5% |

To the carrier system and essential oils composition is added:
Antifungal Medications (Percentages Relative to Total Amount of Carrier System and Essential Oils Composition Above):

| Ciclopirox olamine | 2% |
|---|---|
| Terbinafine | 2% |

In an optional embodiment, the following antifungal medications are further combined with the above (with the percentages also relative to total amount of carrier system and essential oils composition above):

| Tolnaftate | 2% |
|---|---|
| Fluconazole | 2% |

An alternative preferred composition containing none of the additional essential oils includes 5% turpentine (pine oil), 90% mineral oil, 2.5% ciclopirox olamine and 2.5% terbinafine (as terbinafine HCl).

The invention claimed is:

1. An antifungal liquid composition for topical administration to a subject's nail for penetration through the nail, consisting essentially of:
   a carrier system consisting of a turpentine and mineral oil, and optionally one or more members selected from peppermint oil, and essential oil alcohols; and
   an effective amount of one or more active agents selected from the group consisting of ciclopirox olamine and terbinafine, and optionally up to 10 wt % of one or more additional agents selected from the group consisting of tolnaftate, microconazole, itraconazole, ketoconazole, econazole, and fluconazole;
   and optionally from 1 to 5 wt % of one or more antifungal essential oils selected from the group consisting of eucalyptus globulus, eucalyptus citroidora, camphor oil, tea tree oil, manuka oil, anise oil, grapeseed oil, cedarwood atlas oil, lavender spika oil, sage oil, clove oil, and cinnamon oil,
   wherein the turpentine is present in an amount of from 0.1 to 5 wt %, peppermint oil and essential oil alcohols, when present, are in an amount of from 0.1 to 5 wt %, with mineral oil forming the remainder of the composition.

2. The antifungal liquid composition of claim 1, wherein the carrier system contains peppermint oil.

3. The antifungal liquid composition of claim 1, wherein the one or more active agents are a combination of ciclopirox olamine and terbinafine.

4. The antifungal liquid composition of claim 3, wherein the one or more active agents contains tolnaftate.

5. The antifungal liquid composition of claim 3, wherein the one or more active agents contains fluconazole.

6. The antifungal liquid composition of claim 3, wherein the one or more active agents contains econazole.

7. The antifungal liquid composition of claim 4, contains econazole.

8. The antifungal liquid composition of claim 4, contains fluconazole.

9. The antifungal liquid composition of claim 7, contains fluconazole.

10. The antifungal liquid composition of claim 1, containing the one or more antifungal essential oils.

11. The antifungal liquid composition of claim 10, wherein the one or more antifungal essential oils are at least one member selected from eucalyptus globulus and eucalyptus citroidora.

12. The antifungal liquid composition of claim 10, wherein the one or more antifungal essential oils contains one or more members selected from the group consisting of camphor oil, tea tree oil, manuka oil, anise oil, grapeseed oil, cedarwood atlas oil, lavender spika oil, sage oil, clove oil, and cinnamon oil.

13. The antifungal liquid composition of claim 1, wherein the carrier system consists of a combination of turpentine, peppermint oil and mineral oil.

14. The antifungal liquid composition of claim 13, wherein the carrier system contains the one or more essential oil alcohols.

15. The antifungal liquid composition of claim 1, wherein the composition further contains a nail polish.

16. A method for the treatment of fungal infection, comprising:

topically applying to an area of skin or nail in need thereof, an effective amount of the composition as claimed in claim 1.

17. The method of claim 16, wherein said composition is topically applied to an area of nail in need thereof.

18. The method of claim 17, wherein said topically applying forms the thin film of said composition on an entire surface of the nail.

19. The antifungal liquid composition for topical administration according to claim 1, wherein the active agent contains ciclopirox olamine.

20. The antifungal liquid composition for topical administration according to claim 1, wherein the one or more active agents selected from the group consisting of ciclopirox olamine and terbinafine are present in an amount of from 0.1 to 10 wt %.

21. The antifungal liquid composition for topical administration of claim 1, wherein the composition consists essentially of 5 wt % turpentine, 90 wt % mineral oil, 2.5 wt % ciclopirox olamine and 2.5 wt % terbinafine, as terbinafine HCl.

22. The antifungal liquid composition for topical administration of claim 1, wherein the carrier system contains the mineral oil and turpentine in a ratio of mineral oil:turpentine of from 2.5:1 to 18:1.

* * * * *